(12) United States Patent
Fard et al.

(10) Patent No.: US 6,817,996 B2
(45) Date of Patent: Nov. 16, 2004

(54) LIPOSUCTION CANNULA

(75) Inventors: Mike Fard, Charlottesville, VA (US);
Christopher J. Hudson, Dumfries, VA (US); Daniel L. McCombs, Charlottesville, VA (US)

(73) Assignee: Microaire Surgical Instruments, Inc., Charlottesville, VA (US)

( * ) Notice: Subject to any disclaimer, the term of this patent is extended or adjusted under 35 U.S.C. 154(b) by 210 days.

(21) Appl. No.: 10/003,204

(22) Filed: Dec. 6, 2001

(65) Prior Publication Data

US 2003/0125681 A1 Jul. 3, 2003

(51) Int. Cl.[7] ................................................ A61M 1/00
(52) U.S. Cl. ........................ 604/542; 604/22; 604/902
(58) Field of Search ....................... 604/542, 902, 604/27, 28, 35, 43, 239, 280, 167.02, 256, 19, 22

(56) References Cited

U.S. PATENT DOCUMENTS

| 5,052,999 A | * 10/1991 | Klein ............................ 604/19 |
| 5,645,540 A | 7/1997 | Henniges et al. |
| 5,817,050 A | * 10/1998 | Klein ............................ 604/35 |
| 5,830,198 A | 11/1998 | Henniges et al. |
| 6,106,516 A | * 8/2000 | Massengill ..................... 606/15 |
| 6,235,010 B1 | 5/2001 | Wilkinson et al. |
| 6,716,194 B1 | 4/2004 | Cimino et al. |

FOREIGN PATENT DOCUMENTS

| EP | 0509131 | * 10/1992 | ............ A61B/17/22 |
| FR | 2 782 645 | * 8/1998 | ............ A61M/1/00 |

* cited by examiner

Primary Examiner—John J. Calvert
Assistant Examiner—Michele Kidwell
(74) Attorney, Agent, or Firm—McGuireWoods LLP (57) ABSTRACT

A cannula having a bore extending along a length thereof. The cannula includes a vent hole. A plug with an air passage may be inserted within the vent hole such that the air passage is in fluid communication with the bore of the cannula.

21 Claims, 9 Drawing Sheets

LIPOSUCTION CANNULA

BACKGROUND OF THE INVENTION

1. Field of the Invention

The present invention relates generally to a liposuction cannula system and, more particularly, to a liposuction cannula system having a vent hole for increasing the mass flow rate of fatty tissue and other debris through the cannula system.

2. Background Description

Liposuction is a well known surgical procedure for surgically removing fat tissue from selected portions of a patient's body. That is, liposuction may be used, for example, to contour selected body parts such as the abdomen, buttocks, hips, thighs and the like. Liposuction is also known as suction lipectomy, lipolysis and body contour surgery or body sculpting surgery.

To perform this surgical procedure, a hand-held instrument (e.g., a cannula) is inserted through the patient's skin into the fat pockets. Once inserted below the skin and into the fat pockets, the cannula is moved around to break up the fat cells and pieces of the fat tissue are then aspirated through small openings along the sides or tip of the cannula by vacuum pressure from a syringe or pump. The fat tissue is then forced through a central lumen in the cannula to a tissue canister placed in-line with the cannula and the suction source.

The cannula is conventionally a thin tube with an aspirator tip at a remote end. The aspirator tip may include small openings at the sides or end of the tip and is designed to create passages between the tissue and the central lumen of the cannula. The central lumen is then in fluid communication with a suction source so that tissue and fluids can be aspirated or suctioned through the cannula and into the tissue cannister. The suction causes the tissue to be pulled into the openings at the aspirator tip of the cannula. As such, the cannula servers two purposes; namely, the cannula is used to crush, tear, or avulse the fatty tissue and then suction the fatty tissue through the central lumen to aspirate the tissue fragments and fluids from the operative site.

It has been found, however, that conventional cannula systems do not provide adequate mass flow rates for the fatty tissue to pass through the central lumen in order to adequately aspirate the fatty tissue and other fluids from the surgical site. This is mainly due to the fact that a seal is created between the outer surface of the cannula about and along its length and the fatty tissue which prevents the flow of any ambient pressure fluid, such as air, to the operative site about the tip of the cannula. Thus, when suction is applied by a vacuum or other source, the seal prevents the flow of any ambient pressure fluid to the operative site about the tip or the cannula and hence the pressure about the tip of the cannula quickly drops to the pressure of the suction source. This pressure is significantly below the ambient pressure which, in combination with the seal, reduces the suction capacity of the cannula system. In this case, the fatty tissue fragments and other fluids move very slowly through the cannula and suction tubing.

To avoid this problem, the tip of the cannula may be withdrawn from the patient so that the seal is broken and the tip or side openings are exposed to ambient air pressure. To accomplish this, however, the surgeon has to insert and remove the cannula from the surgical site many times during a surgical procedure. This may lead to further trauma at the surgical site.

To avoid inserting and removing the cannula from the surgical site to thus increase the mass flow rate of the fatty tissue, other systems have provided a single hole or vent in the hub portion of the cannula. The hole provides an air passage into the system and thus aids in the suctioning of the fatty tissue and other fluids. These systems, however, typically require a surgeon to regulate the air flow through the hole by manipulating the surgeon's finger over the hole.

The use of a vent hole in prior art cannulas is both cumbersome and inefficient. With regard to the former shortcoming, the surgeon must both manipulate the cannula and, at the same time, attempt to regulate the air flow which is delivered through the hole. As to the latter shortcoming, the surgeon cannot regulate the air flow through the hole with any accuracy. These same systems do not provide a mechanism for allowing the airflow to be delivered parallel to the liquid flow and away from the cannula wall. That is, the airflow in these systems are introduced into the lumen in a turbulent flow thus disrupting the liquid flow therein. Also, these systems have not provided the vent holes, either in position or size, to maximize the suctioning capabilities of the cannula system, nor do they make any accommodations for clogging of the hole, itself.

Accordingly, there remains a need to provide a cannula system which provides a mechanism to maximize the suctioning of the fatty tissue and other debris and fluid. Also, there remains a need to provide a system which is capable of introducing air flow into the lumen in a path that is parallel to the liquid flow and away from the cannula wall, both of which would further maximize the mass flow rate of the fatty tissue, liquid and other debris through the cannula.

SUMMARY OF THE INVENTION

It is therefore an object of the present invention to provide a cannula system which is capable of increasing the mass flow rate of fatty tissue, liquid and other debris flowing through the lumen.

It is another object of the present invention to provide a cannula system which has a mechanism for providing airflow into the lumen of the cannula parallel to the fatty tissue, liquid and other debris flowing therethrough.

It is still a further object of the present invention to provide a cannula system which provides airflow into the lumen of the cannula and away from the interior wall of the cannula.

It is also a further object of the present invention to provide a cannula system which is capable of introducing airflow into the lumen in a non-turbulent manner.

In one aspect of the invention, a cannula system has a tube having a bore extending along a length thereof. An assembly is connected to a proximal end of the tube and an aspirator tip having openings is positioned at another end of the tube remote from the assembly. A vent hole is positioned along the length of the tube away from the assembly. The vent hole has a diameter of approximately between 0.012 and 0.0135 inches and allows air to flow within the bore of the tube. In embodiments, the vent hole is positioned at substantially a center of the tube to prevent clogging thereof.

In another aspect of the present invention, a cannula system includes a tube having a bore extending along a length thereof and an aspirator tip having openings positioned at a remote end of the tube and in fluid communication with the bore. A vent hole is positioned along the length of the tube and a plug is positioned within the vent hole. The plug has an air passageway in fluid communication with the bore.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENT OF THE INVENTION

The present invention is directed to a cannula system with a vent hole which significantly improves the mass flow rate of liquid, fat tissue and other debris during a liposuction procedure. In one embodiment, the cannula system is designed in such a manner that airflow is introduced into the lumen of the cannula parallel to the flow of the liquid, fat tissue and other debris. This arrangement prevents turbulent mixing of the airflow with the fat tissue, liquid and other debris, and hence increases the efficiency of the cannula system. In other embodiments, the cannula system is designed with a vent hole having a position and diameter which maximizes the mass flow rate of fat tissue, liquid and the like therethrough while minimizing any clogging of the hole. The position and diameter of the vent hole for maximizing the mass flow rate is based on extensive experimentations and testings with materials having substantially the same density and viscosity as fat tissue. The cannula system of the present invention thus allows a surgeon to perform liposuction procedures in a more efficient manner due to an increased mass flow rate of fat tissue, liquid and other debris through the lumen of the cannula.

Cannula System

Figure 1:
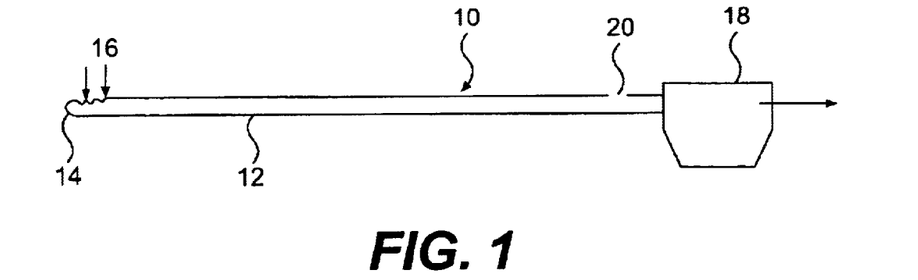
FIG. 1 shows a plan view of a cannula system of the present invention.

Referring now to the drawings, and more particularly to FIG. 1, there is shown a plan view of a cannula system of the present invention generally depicted as reference numeral 10. The cannula system 10 includes a tube 12 having a bore along a length thereof (i.e., defining a lumen). The tube 12 (hereinafter referred to as a hollow tube) includes an aspirator tip 14 having openings 16 for the aspiration of fat tissue and other debris and liquid from a surgical site. At a remote end of the aspirator tip 14 is a hub or connector assembly 18 which is mounted to a surgical tool and a suctioning device (not shown). The hub or connector assembly 18 may also represent a handle for use in manual systems. The suctioning device may be a vacuum or syringe used to provide a suctioning of the fat tissue, debris and the like from the surgical site via the openings 16 and bore of the hollow tube 12.

A vent hole 20, in fluid communication with the bore of the hollow tube 12, is positioned along the length of the hollow tube 12. In a preferred embodiment, the vent hole 20 is placed remote from the hub or handle 18 and more specifically at approximately a center of the cannula along a length thereof. The placement of the vent hole 20 at the center of the cannula decreases the clogging of the vent hole by fat tissue or other debris during the surgical procedure. Also, the vent hole 20 permits air to be suctioned into and through the hollow tube 12 thus increasing the mass flow rate of the liquid, fat tissue and the like through the cannula system. In the preferred embodiment, the diameter of the vent hole is approximately between 0.012 and 0.0135 inches which provides a maximum mass flow rate; however, other diameter vent holes depending on the viscosity of the fat tissue, liquid and other debris may also be used with the present invention.

Figure 2:
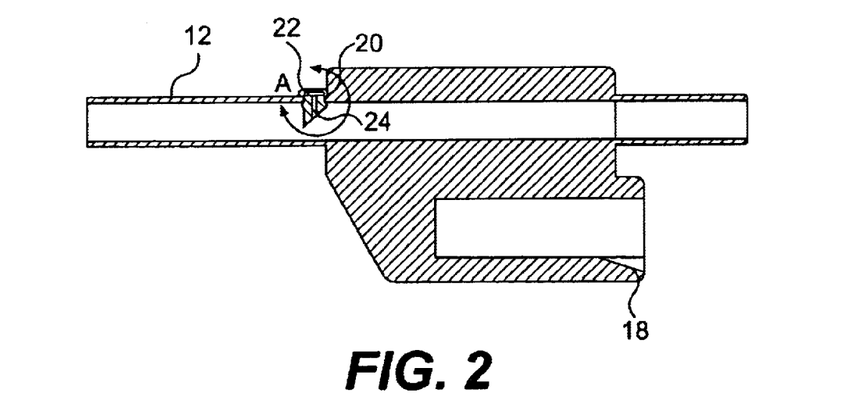
FIG. 2 shows an exploded view of the cannula system with a plug in the vent hole.
Figure 8:
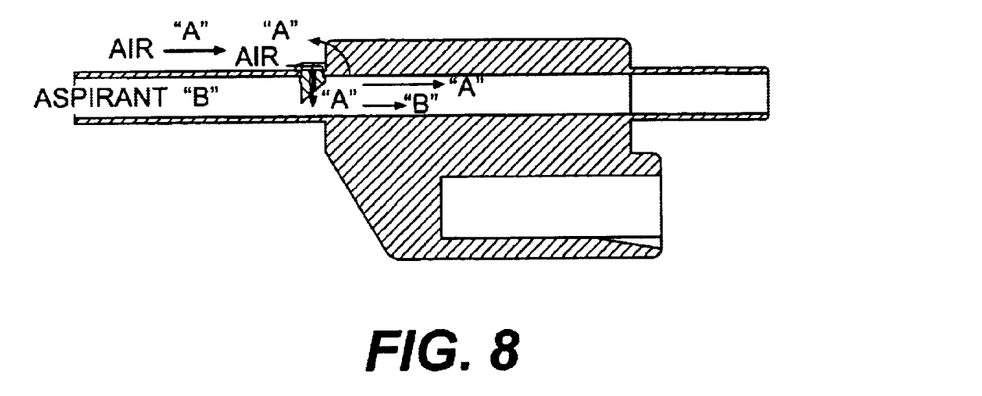
FIG. 8 shows a diagram of the air flow in the cannula system of the present invention.

FIG. 2 shows an exploded view of the cannula system with a plug in the vent hole 20. In this view, the plug 22 is inserted within the vent hole 20 and includes an air passageway 24 which is in fluid communication with the bore of the hollow tube 12 and hence permits airflow to flow directly into the flow of the liquid, fat tissue and the like being suctioned through the hollow tube 12. The plug 22, which is pressed into the vent hole 20, reduces losses caused by air making a right angle turn and turbulently mixing with the flow of the liquid, fat tissue and the like being suctioned through the hollow tube 12. The plug 22 additionally keeps the airflow away from the interior wall of the cannula. Taking into account the vent hole 20 or the combination of the vent hole 20 and the plug 22, it was found that the mass flow rate through the cannula system of the present invention is increased compared to a cannula as shown with reference to at least FIG. 8.

Figure 3:
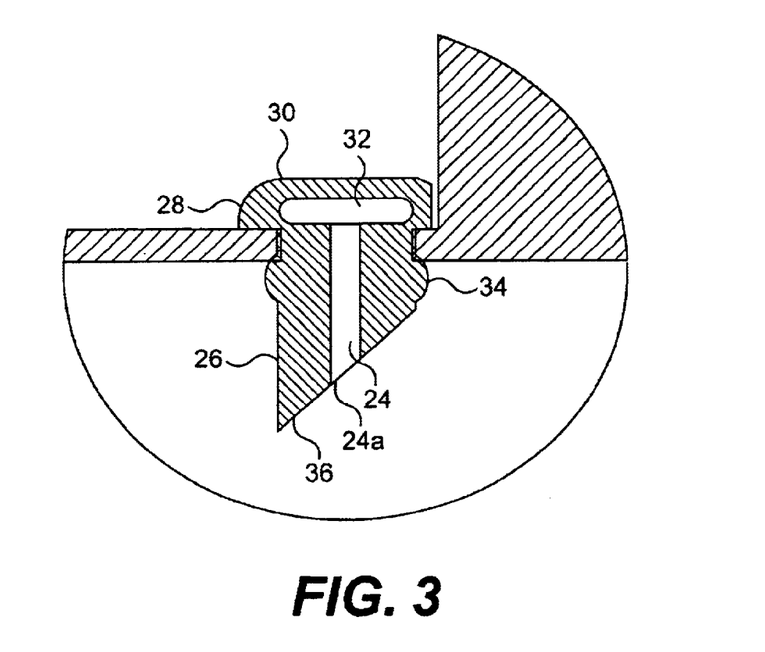
FIG. 3 shows an exploded view of the plug about section "A" of FIG. 2.

FIG. 3 shows an exploded view of the plug 22 used with the cannula system of the present invention. The plug 22 includes a substantially cylindrical section 26 and a collar portion 28 having a closed end or hood 30 which includes at least one opening 32 in fluid communication with the passageway 24. The at least one opening 32 of the hood 30, in the aggregate, is preferably equal to or larger than the opening 24a of the passageway 24. The at least one opening 32 also allows for the passage of air between ambient and the opening 24a which, in turn, is directed within the hollow portion of the cannula. The hood 30 prevents debris from entering the passageway and clogging the opening 24a or the passageway 24. Also, in the embodiments, the opening 24a is preferably approximately between 0.012 and 0.0135 inches in diameter while the vent hole 20 is approximately the same diameter or slightly larger in order to accommodate the cylindrical section 26 of the plug. The configuration of the plug 22 allows the surgeon to use the cannula system of the present invention without the need to adjust the flow rates by plugging or impeding the incoming air flow with the surgeon's finger or other instrument.

Still referring to FIG. 3, a dimple or bulging portion 32 is provided about the cylindrical section 26, and is placed a distance apart from the collar portion 28 such that the wall of the cannula is positioned between the collar portion 28 and the bulging portion 34. That is, the the collar portion 28 and the bulging portion 34 are spaced apart in order to lock or retain the plug about the wall portion of the cannula and, hence, the opening 24a of the plug 22 within the airflow of the cannula. In embodiments, the cylindrical section 26 has a tapered end 36 which reduces drag within the hollow tube 12 portion of the cannula. Also, the collar portion 28 is preferably larger than the air passageway 24. During use, a negative pressure is created within the passageway which keeps the opening 24a and passageway 24 open during the suctioning of fatty tissue and the like.

Figures 4, 5:
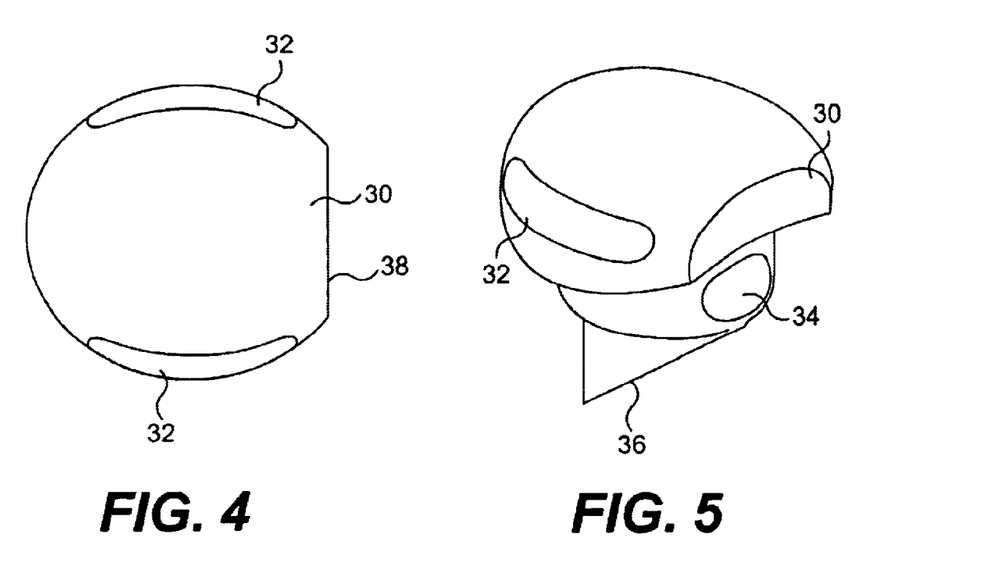
FIG. 4 shows a top view of the plug used with the cannula system of the present invention.
FIG. 5 shows a perspective view of the plug.

FIG. 4 shows a top view of the plug. In this view, the at least one opening 32 is two openings. However, more than two openings, depending on the sizes thereof, are also contemplated for use with the plug 22. In embodiments, a flat portion 38 is provided on the hood 30 which may be in alignment with the hub of the cannula in order to align the plug 22 within the hole and further prevent the plug 22 from rotating when air flow is passing through the hollow portion 12 of the cannula. This aspect of the present invention is shown clearly in FIG. 3; however, it is also noted that the flat portion 38 may not be needed for alignment or preventing rotation of the plug 22 due to the fact that the cylindrical section 26 and/or the combination of the collar portion 28 and the bulging portion 34 will "lock" the plug within the venting hole 20 of the cannula.

FIG. 5 shows a perspective view of the plug 22. The bulging portion 34 is provided on the cylindrical portion 26 and the at least one opening 32 is provided on the hood 30. In embodiments, the at least one opening 32, as shown in more detail in both FIGS. 5 and 6, is positioned substantially perpendicular to the passageway 24.

Figure 6:
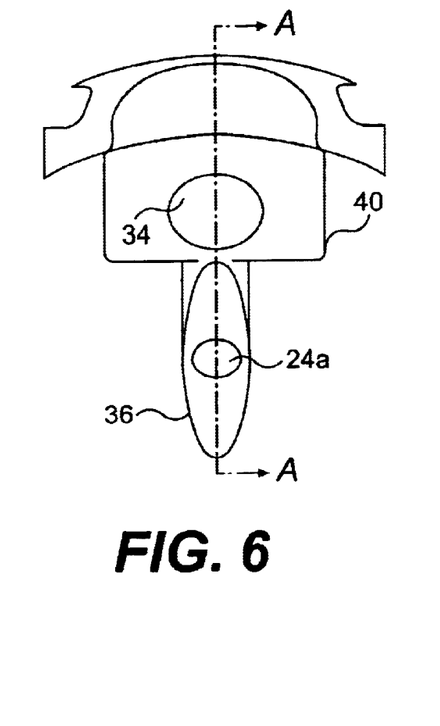
FIG. 6 shows another embodiment of the plug used with the present invention.

FIG. 6 shows another embodiment of the plug 22. In this embodiment, the taper portion 36 extends from a tip of the cylindrical portion 26 to a larger diameter cylindrical section 40. The larger diameter cylindrical section 40 includes the bulging portion 34. The larger diameter portion 40 is approximately the size the vent hole 20 of the cannula which ensures an air tight fit thereon. The bulging portion 34 still acts as a mechanism, in conjunction with the collar portion 28, to retain the plug on the cannula, itself.

Figure 7:
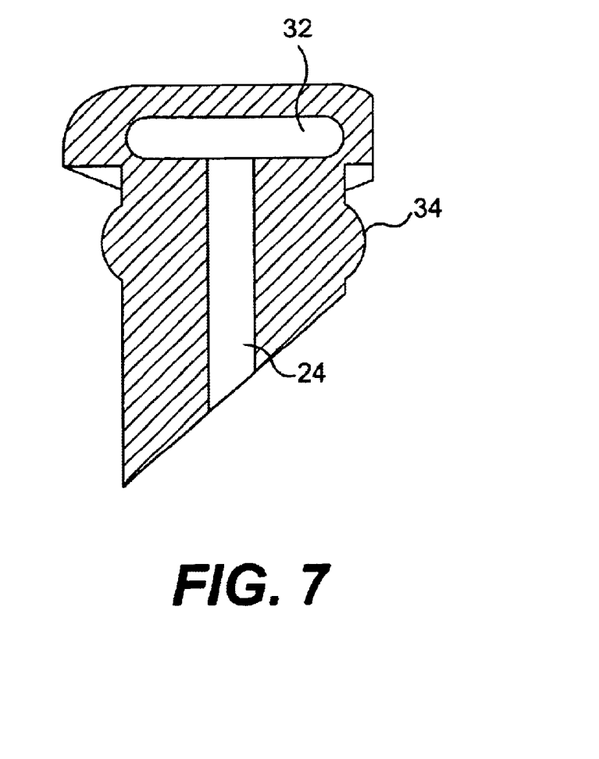
FIG. 7 shows a cut-away view of the plug.

FIG. 7 shows a diagram of the airflow through the cannula 10 of the present invention. As shown, the air flow, depicted as arrows "A", is introduced into the hollow interior portion of the cannula parallel to the aspirant flow, depicted as arrows "B". This introduction of the air flow substantially eliminates any turbulent mixing of the air with the aspirant within the hollow tube 12. This is mainly due to the fact that the plug 22 and more particularly the air passageway 24 extends within the hollow tube 12 thus directing the air flow directly into the stream of the aspirant (i.e., fat tissue, liquid and other debris). As further shown, the air flow will stay away from the interior walls of the interior portion of the hollow tube 12 due to the configuration of the plug 22.

Figure 9:
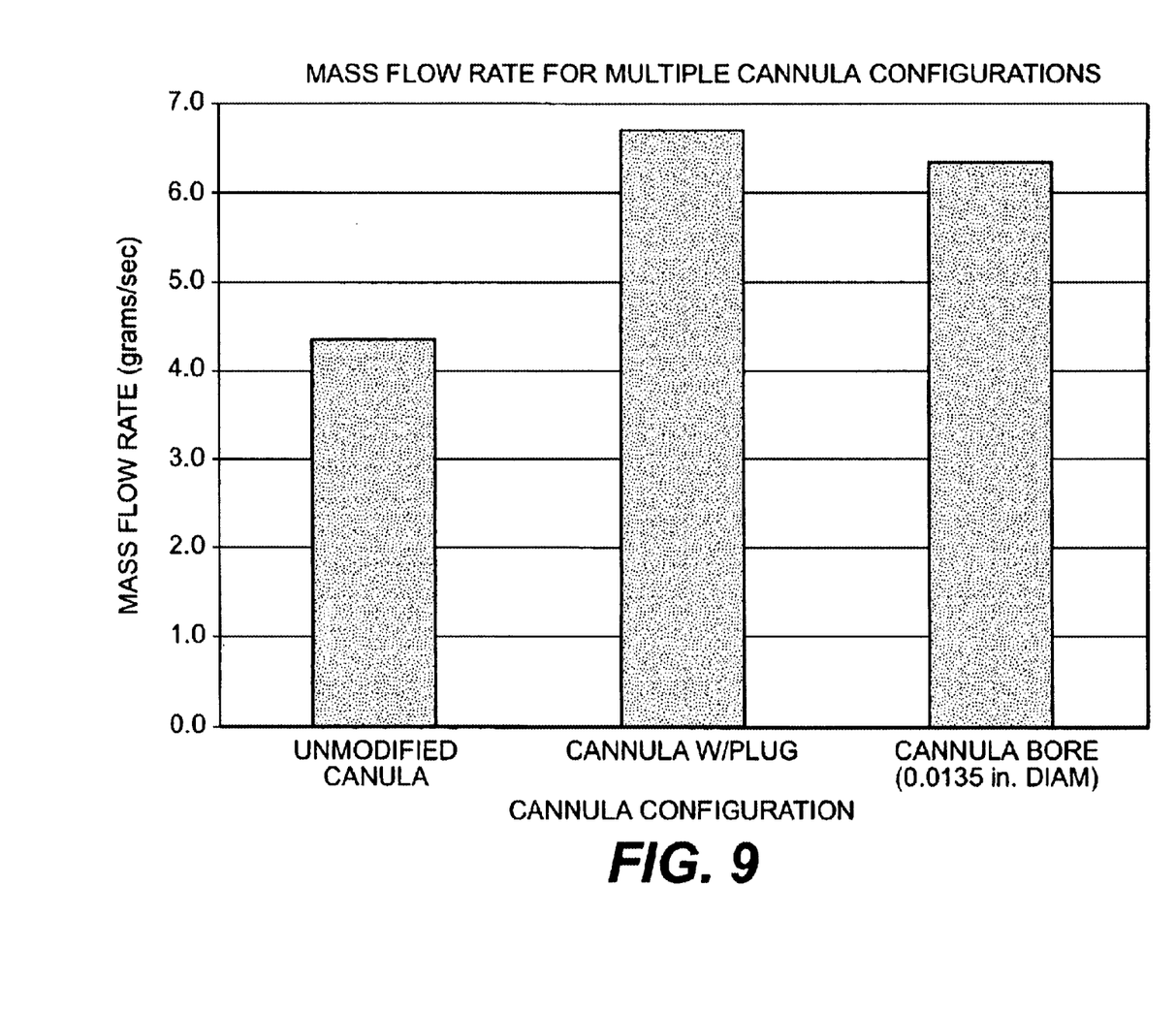
FIG. 9 shows a comparison of a mass flow rate for multiple cannula configurations.

FIG. 9 shows a cannula mass flow rate with expected trend. It is shown in this graph that the cannula system with the plug has the most efficient flow rate in grams/second (approximately 6.5 grams/second). Second, the cannula system with the vent hole (with a diameter of approximately 0.0135 inches) has the second most efficient flow rate in grams/second (6.2 grams/second). The least efficient flow rate was an unmodified cannula (i.e., a cannula with no vent hole or plug).

Experiments and Test Results

Extensive experimentation and testing was performed in order to find the most advantageous vent hole size and placement thereof. It has been found through these extensive experiments and testings that a vent hole of approximately between 0.012 to 0.0135 inches in diameter maximizes the mass flow rate of the fat tissue and the like within the lumen of the cannula during suctioning. It has also been further found through these experiments and extensive testing that a plug used to direct the air flow directly into and parallel with the fat tissue, liquid and other debris within the lumen also maximizes the mass flow rate of such materials. Additionally, the placement of the hole within the center of the cannula along its length will also prevent clogging of the vent hole by such material. The results of these extensive testings and experiments are discussed below with reference to the tables and FIGS. 9 through 13. The test materials (aspirant) used with these experiments is consistent with the viscosity and density of fat tissue.

Figure 10:
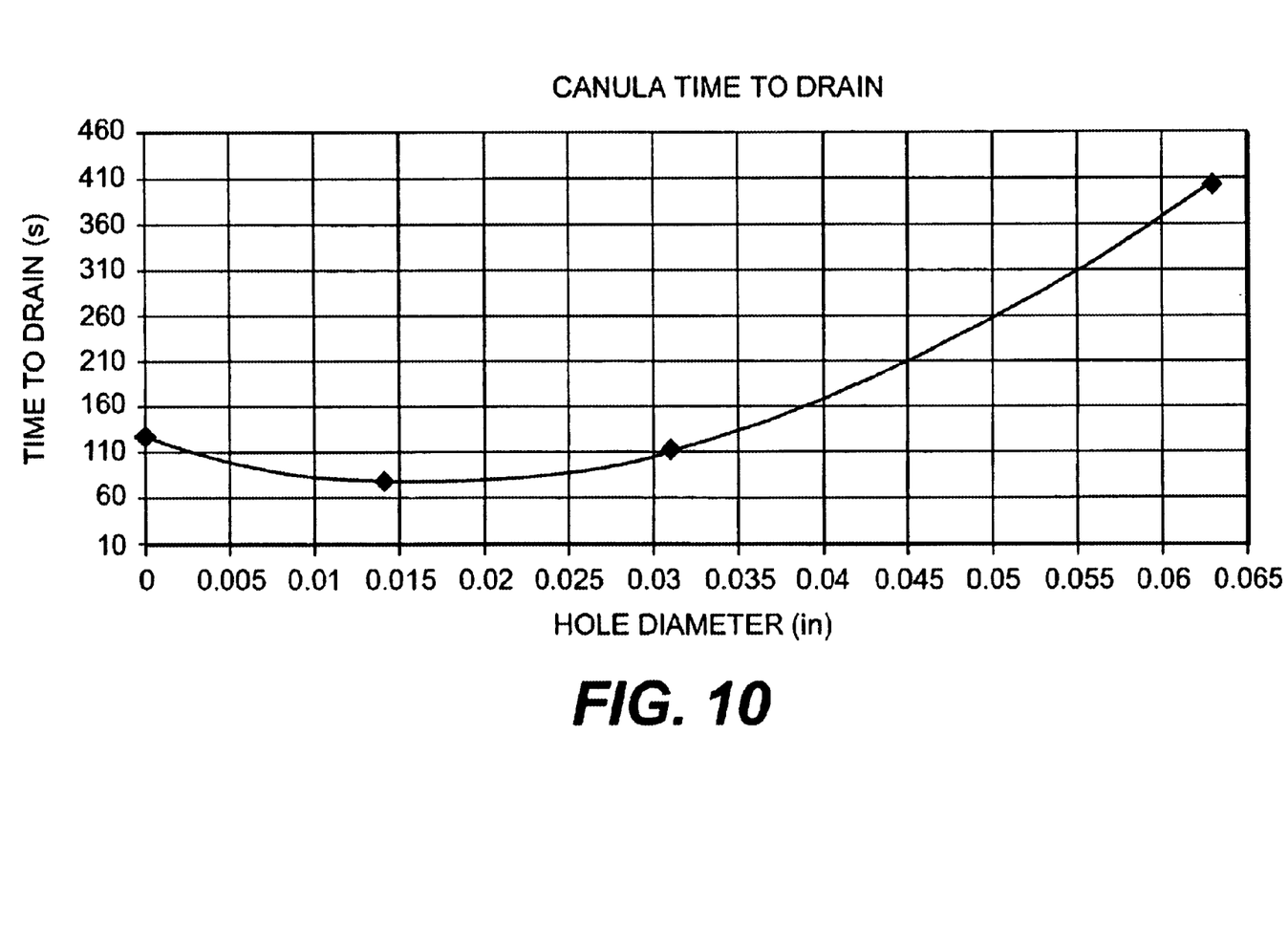
FIG. 10 shows a graph representative of the results shown in Table 1.

By way of a first experiment, Table 1 shows the time to drain 400 ml of fluids in seconds over a range of several different diameter vent holes. It was determined that approximately a 0.014 inch diameter and more specifically approximately 0.012 to 0.0135 inches diameter vent hole maximized the mass flow rate of the testing material through the cannula system. FIG. 10 graphically shows the results of table 1.

TABLE 1

| Diameter | | time to drain 400 ml (s) | | | | Avg |
|---|---|---|---|---|---|---|
| (in) | Diam. Ratio | 1 | 2 | 3 | 4 | Time(s) |
| 0 | 0.000 | 125 | 134 | 124 | 121 | 126.0 |
| 0.011 | 0.068 | 100 | 98 | 101 | 98 | 99.3 |
| 0.014 | 0.087 | 79 | 80 | 74 | 80 | 78.3 |
| 0.016 | 0.099 | 87 | 88 | 89 | 87 | 87.8 |
| 0.022 | 0.137 | 96 | 91 | 96 | 91 | 93.5 |
| 0.031 | 0.193 | 116 | 110 | 113 | 118 | 114.3 |
| 0.063 | 0.391 | 390 | 394 | 412 | 428 | 406.0 |

In calculating the results of Table 1, the following were taken into consideration:

$y = -563277 \times 3 + 203682 \times 2 - 6151.9 \times + 126$ $T = -563277 \times D^3 + 203682 \times D^2 + -6151.9 \times D + 126$ $dT/dD = -1689831 \times D^2 + 407364 \times D + -6151.9$ $dT/dD = 2.66E{-}08$ at $D = 0.0162$ min $T = 77.4$ at $D = 0.0162$ where D is diameter and T is time. This calculation is representative of the parabolic line shown in FIG. 10 (i.e., a min time of 77.4 translates to a diameter of 0.0162).

Table 2 shows the results of an experiment using pure test surgical aspirant (100% test surgical aspirant material) having a density of 1284 kg/m$^3$.

TABLE 2

| Diameter | Diam. | | time (s) | | Avg Time | Mass flow rate |
|---|---|---|---|---|---|---|
| (in) | Ratio | 1 | 2 | 3 | (s) | (g/s) |
| 0 | 0.000 | 615 | 620 | 612 | 615.7 | 0.834 |
| 0.014 | 0.087 | 175 | 192 | 178 | 181.7 | 2.827 |
| 0.031 | 0.193 | 250 | 241 | 243 | 244.7 | 2.099 |
| 0.063 | 0.391 | 1026 | 1070 | 1104 | 1066.7 | 0.482 |

Table 3 shows the results of an experiment using 90% test surgical aspirant by volume having a density of 1256 kg/m$^3$.

TABLE 3

| Diameter (in) | Diam. Ratio | time (s) 1 | 2 | 3 | Avg Time (s) | Mass flow rate (g/s) |
|---|---|---|---|---|---|---|
| 0 | 0.000 | 418 | 426 | 427 | 423.7 | 1.185 |
| 0.014 | 0.087 | 154 | 152 | 150 | 152.0 | 3.304 |
| 0.031 | 0.193 | 192 | 198 | 202 | 197.3 | 2.545 |
| 0.063 | 0.391 | 756 | 798 | 830 | 794.7 | 0.632 |

Table 4 shows the results of an experiment using 80% test surgical aspirant by volume having a density of 1227 kg/m³.

TABLE 4

| Diameter (in) | Diam. Ratio | time (s) 1 | 2 | 3 | Avg Time (s) | Mass flow rate (g/s) |
|---|---|---|---|---|---|---|
| 0 | 0.000 | 282 | 275 | 276 | 277.7 | 1.768 |
| 0.014 | 0.087 | 116 | 115 | 117 | 116.0 | 4.232 |
| 0.031 | 0.193 | 166 | 167 | 168 | 167.0 | 2.939 |
| 0.063 | 0.391 | 596 | 626 | 614 | 612.0 | 0.802 |

Table 5 shows the results of an experiment using 70% test surgical aspirant by volume having a density of 1199 kg/m³.

TABLE 5

| Diameter (in) | Diam. Ratio | time (s) 1 | 2 | 3 | Avg Time (s) | Mass flow rate (g/s) |
|---|---|---|---|---|---|---|
| 0 | 0.000 | 175 | 183 | 181 | 179.7 | 2.669 |
| 0.014 | 0.087 | 96 | 99 | 101 | 98.7 | 4.860 |
| 0.031 | 0.193 | 135 | 138 | 139 | 137.3 | 3.492 |
| 0.063 | 0.391 | 472 | 480 | 486 | 479.3 | 1.000 |

Table 6 shows the results of an experiment using 100% water by volume having a density of 1000 kg/m³.

TABLE 6

| Diameter (in) | Diam. Ratio | time (s) 1 | 2 | 3 | Avg Time (s) | Mass flow rate (g/s) |
|---|---|---|---|---|---|---|
| 0 | 0.000 | 43 | 41 | 42 | 42.0 | 9.524 |
| 0.014 | 0.087 | 60 | 59 | 55 | 58.0 | 6.897 |
| 0.031 | 0.193 | 84 | 82 | 83 | 83.0 | 4.819 |
| 0.063 | 0.391 | 472 | 472 | 472 | 472.0 | 0.847 |

Table 7 shows the mass flow rates for a given hole diameter based on certain percentages of the test surgical aspirant.

TABLE 7

| Percent of test aspirant | Mass Flow Rates for a given Hole Diameter (in) | | | |
|---|---|---|---|---|
| | 0 | 0.014 | 0.031 | 0.063 |
| 0 | 9.524 | 6.897 | 4.819 | 0.847 |
| 70 | 2.669 | 4.860 | 3.492 | 1.000 |
| 80 | 1.768 | 4.232 | 2.939 | 0.802 |
| 90 | 1.185 | 3.304 | 2.545 | 0.632 |
| 100 | 0.834 | 2.827 | 2.099 | 0.482 |

Figure 14:
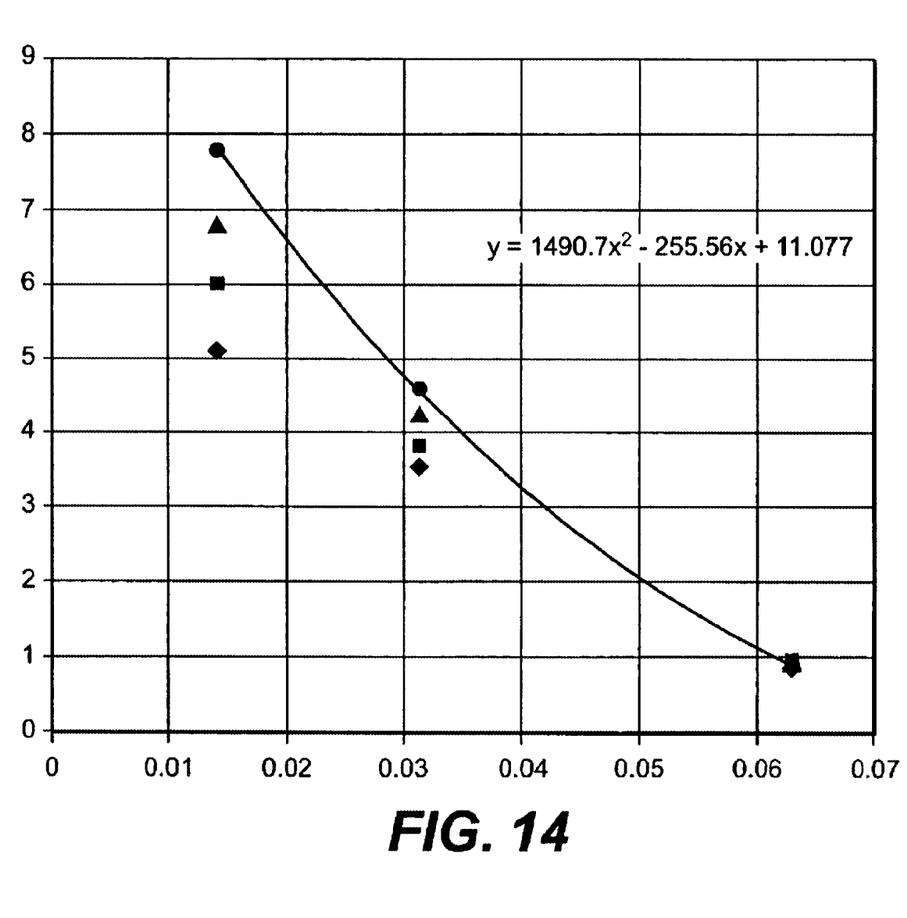
FIG. 14 shows graphical results represented by Table 8.

Table 8 shows the results of an experiment using a pure test surgical aspirant. In this case, the initial m=170.82 and b=0.834. Also, the final m=−60.66 and b=4.303. Additionally, n=3.819402. The variable "m" is an initial slope and "n" is a curve blend exponent, and variable "b" represents "y" intercepts as shown in the graph of FIG. 14.

TABLE 8

| Diam | initial | final | blend | error | error2 | rms |
|---|---|---|---|---|---|---|
| 0 | 0.834 | 4.3033 | 0.833803 | 0.000 | 1.71684E−07 | 0.154763 |
| 0.0025 | 1.261 | 4.1516 | 1.257811 | | | |
| 0.005 | 1.688 | 4.0000 | 1.672312 | | | |
| 0.0075 | 2.115 | 3.8483 | 2.062412 | | | |
| 0.01 | 2.542 | 3.6966 | 2.403517 | | | |
| 0.0125 | 2.970 | 3.5450 | 2.66654 | | | |
| 0.014 | 3.226 | 3.4540 | 2.77775 | −0.049 | 0.002440944 | |
| 0.015 | 3.397 | 3.3933 | 2.831502 | | | |
| 0.0175 | 3.824 | 3.2417 | 2.898978 | | | |
| 0.02 | 4.251 | 3.0900 | 2.887316 | | | |
| 0.0225 | 4.678 | 2.9384 | 2.820439 | | | |
| 0.025 | 5.105 | 2.7867 | 2.718623 | | | |
| 0.0275 | 5.532 | 2.6350 | 2.595875 | | | |
| 0.03 | 5.959 | 2.4834 | 2.460909 | | | |
| 0.031 | 6.130 | 2.4227 | 2.404741 | 0.306 | 0.093365795 | |
| 0.0325 | 6.386 | 2.3317 | 2.31888 | | | |
| 0.035 | 6.813 | 2.1801 | 2.172775 | | | |
| 0.0375 | 7.240 | 2.0284 | 2.024312 | | | |
| 0.04 | 7.667 | 1.8768 | 1.874483 | | | |
| 0.0425 | 8.094 | 1.7251 | 1.723864 | | | |
| 0.045 | 8.521 | 1.5734 | 1.572787 | | | |
| 0.0475 | 8.948 | 1.4218 | 1.421447 | | | |
| 0.05 | 9.375 | 1.2701 | 1.26996 | | | |
| 0.0525 | 9.802 | 1.1185 | 1.118389 | | | |
| 0.055 | 10.229 | 0.9668 | 0.966774 | | | |

TABLE 8-continued

| Diam | initial | final | blend | error | error2 | rms |
|---|---|---|---|---|---|---|
| 0.0575 | 10.657 | 0.8151 | 0.815135 | | | |
| 0.06 | 11.084 | 0.6635 | 0.663486 | | | |
| 0.0625 | 11.511 | 0.5118 | 0.511831 | | | |
| 0.063 | 11.596 | 0.4815 | 0.481499 | 0.000 | 4.43149E−13 | |
| 0.065 | 11.938 | 0.3602 | 0.360174 | | | |
| 0.0675 | 12.365 | 0.2085 | 0.208516 | | | |
| 0.07 | 12.792 | 0.0569 | 0.056858 | | | |
| 0.0725 | 13.219 | −0.0948 | #NUM! | | | |
| 0.075 | 13.646 | −0.2465 | #NUM! | | | |
| 0.0775 | 14.073 | −0.3981 | #NUM! | | | |

Table 9 show the percent of the test surgical aspirant to the mass flow rates for a given hole diameter of the vent hole.

TABLE 9

| Percent of test surgical | Mass Flow Rates for a given Hole Diameter (in) | | | |
|---|---|---|---|---|
| aspirant | 0 | 0.014 | 0.031 | 0.063 |
| 0 | 9.524 | 6.897 | 4.819 | 0.847 |
| 70 | 2.669 | 4.860 | 3.492 | 1.000 |
| 80 | 1.768 | 4.232 | 2.939 | 0.802 |
| 90 | 1.185 | 3.304 | 2.545 | 0.632 |
| 100 | 0.834 | 2.827 | 2.099 | 0.482 |

Figure 11:
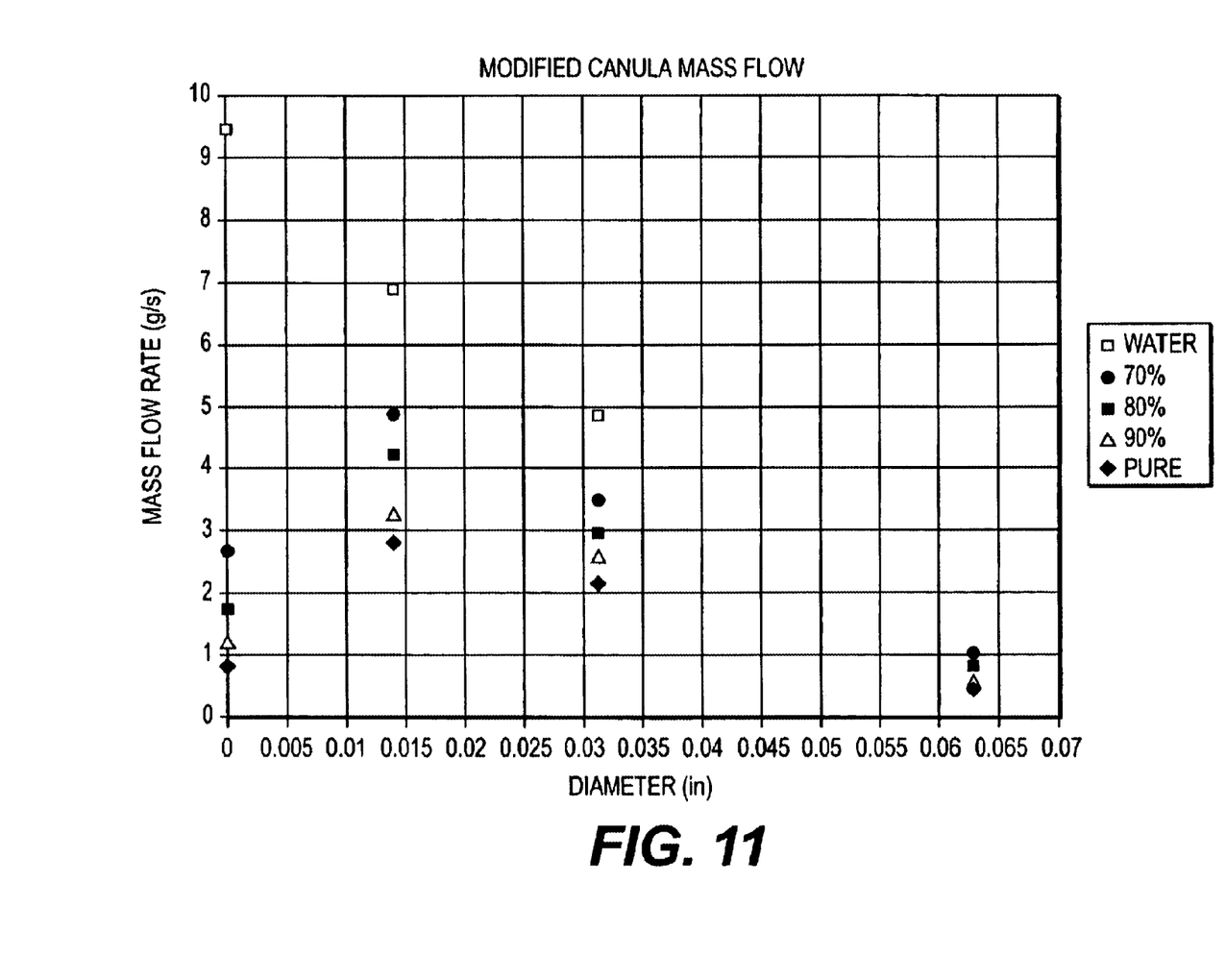
FIG. 11 shows the mass flow rate of the cannula of the present invention using different aspirants.
Figure 12:
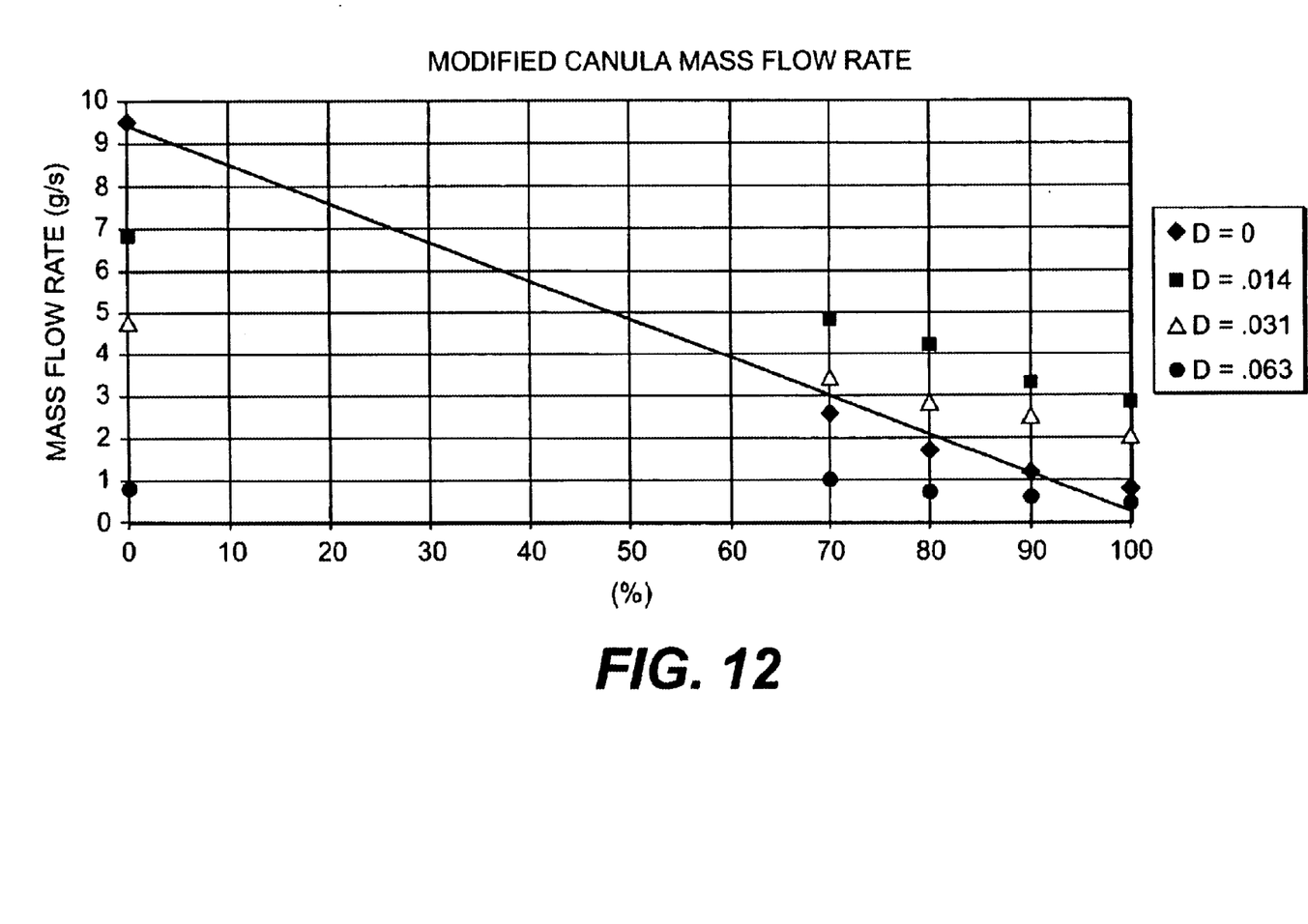
FIG. 12 shows the mass flow rate of a cannula using different sized venting holes.
Figure 13:
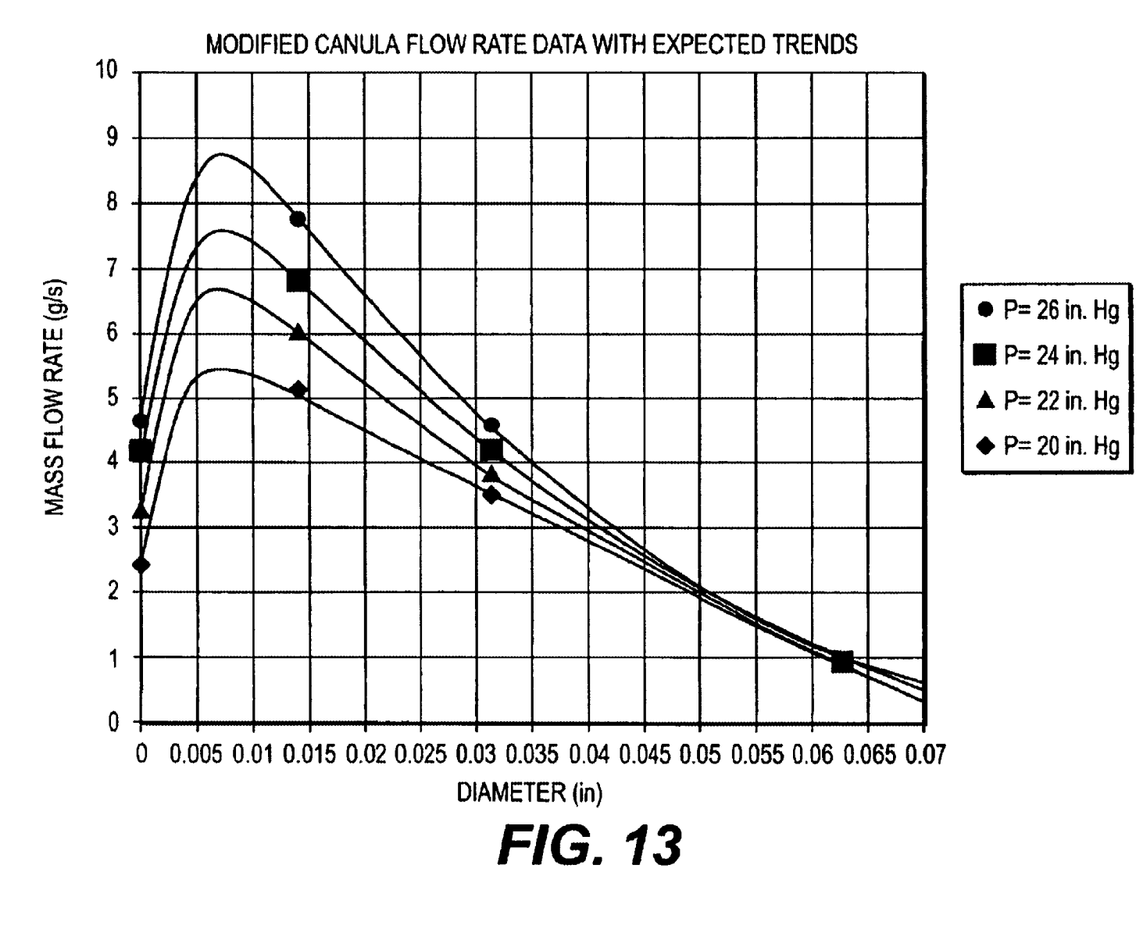
FIG. 13 shows the mass flow rate of the cannula using different pressures.

FIGS. 11 and 12 graphically show the results of tables 2–9. As seen graphically, as a whole, the mass flow rates are greatest for all percentages (100%, 90%, 80% and 70%) of surgical test aspirant at a hole diameter of approximately 0.012 to 0.0135 inches. This coincides with the information presented in tables 2–9.

Further experiments were conducted at various pressures known to be used during liposuction procedures to determine the vent hole diameter which provides the maximum mass flow rate (in grams/second) of test aspirant. The pressures used during these experiments include (i) 20 in. Hg, (ii) 22 in. Hg, (iii) 24 in. Hg and (iv) 26 in. Hg. Again, it was found that a vent hole diameter of approximately 0.012 to 0.0135 inches provides the maximum mass flow rate at these pressures and for the test aspirant. This is shown graphically in FIG. 13.

While the invention has been described in terms of its preferred embodiments, those skilled in the art will recognize that the invention can be practiced with modification within the spirit and scope of the appended claims.

What is claimed is:

1. A cannula system comprising:
   a tube having a bore extending along a length thereof;
   an assembly connecting to a proximal end of the tube;
   an aspirator tip having openings positioned at another end of the tube remote from the assembly; and
   an opening acting as a vent hole positioned along the length of the tube away from the assembly, the vent hole having a diameter of approximately between 0.003 and 0.02 inches and which allows air to flow within the bore of the tube.

2. The cannula system of claim 1, wherein the opening is positioned at substantially a center of the tube to prevent clogging thereof.

3. The cannula system of claim 1, further comprising a plug which extends within the opening.

4. The cannula system of claim 3, wherein the plug introduces air flow into the tube parallel to a flow of aspirant during suctioning via a plug opening, the plug opening acting as the vent hole which has the diameter of approximately between 0.003 and 0.02 inches and which allows air to flow within the bore of the tube.

5. The cannula system of claim 4, wherein the plug further introduces air flow directly into the flow of the aspirant during suctioning.

6. The cannula system of claim 4, wherein the plug includes:
   a cylindrical member having an air passage which leads to the plug opening;
   a collar portion having a closed end which directs air flow into the plug opening; and
   and a bulging portion remote from the collar portion,
   wherein when the plug is inserted within the opening of the tube, the collar acts as a stop by resting on an outer surface of the tube and the cylindrical member is positioned within the bore of the tube such that the plug opening is in substantial alignment with the flow of the aspirant during the suctioning.

7. The cannula of claim 6, further comprising a hood with at least one opening placed over the air passage.

8. The cannula system of claim 1, wherein the opening maximizes a mass flow rate of material having a density of substantially equal to or above 1000 kg/m$^3$.

9. The cannula system of claim 8, wherein the opening maximizes the mass flow rate of material having a density of approximately between 1000 kg/m$^3$ to 1284 kg/m$^3$.

10. The cannula system of claim 1, wherein the assembly is one of a hub assembly adapted for use with a reciprocating cannula system and a handle adapted for use with a manual cannula system.

11. The cannula system of claim 1, wherein the diameter of the hole is approximately between 0.012 and 0.0135 inches.

12. A cannula system comprising:
   a tube having a bore extending along a length thereof;
   an aspirator tip having openings positioned at remote end of the tube and in fluid communication with the bore;
   an opening positioned along the length of the tube; and
   a plug positioned with the opening, the plug having an air passageway in fluid communication with the bore.

13. The cannula system of claim 12, wherein the air passageway is in fluid communication with an opening in the plug.

14. The cannula system of claim 13, wherein the plug opening has a diameter of approximately between 0.012 and 0.0135 inches.

15. The cannula system of claim 12, wherein the plug introduces air flow into the tube parallel to and directly into a flow of aspirant during suctioning.

16. The cannula system of claim 12, wherein the opening is positioned along substantially a center of the tube along a length thereof.

17. The cannula system of claim 12, further comprising a hub remote from the opening.

18. The cannula system of claim 12, wherein the plug reduces losses caused by air making a right angle turn and turbulently mixing with a flow of aspirant suctioned through the tube.

19. The cannula system of claim 18, wherein the at least one hole has an air flow capacity at least equal to an air flow capacity of the opening of the plug.

20. The cannula system of claim 12, wherein the plug includes:

a cylindrical member having the air passageway and an opening; and a collar portion having a closed end which directs air flow into the opening, wherein when the plug is inserted within the opening of the tube, the collar acts as a stop by resting on an outer surface of the tube and the cylindrical member is positioned within the bore of the tube such that the opening of the plug is in substantial alignment with the flow of the aspirant during the suctioning.

21. The cannula system of claim 12, wherein the plug includes a hood with at least one hole placed over the air passage.

* * * * *